United States Patent [19]

Muto

[11] 4,270,529
[45] Jun. 2, 1981

[54] ENDOTRACHEAL TUBE STABILIZER

[76] Inventor: Rudolph Muto, 24 Williams St., Andover, Mass. 01801

[21] Appl. No.: 66,029

[22] Filed: Aug. 13, 1979

Related U.S. Application Data

[63] Continuation-in-part of Ser. No. 23,652, Mar. 26, 1979.

[51] Int. Cl.³ .............................................. A61M 15/00
[52] U.S. Cl. ............................ 128/200.26; 128/207.17
[58] Field of Search ...................... 128/200.26, 207.17, 128/DIG. 26, 207.14–207.16

[56] References Cited

U.S. PATENT DOCUMENTS

| | | | |
|---|---|---|---|
| 2,693,182 | 11/1954 | Phillips | 128/200.26 |
| 3,756,244 | 9/1973 | Kinnear et al. | 128/207.14 |
| 4,068,658 | 1/1978 | Berman | 128/200.26 |
| 4,142,527 | 3/1979 | Garcia | 128/DIG. 26 |
| 4,167,946 | 9/1979 | Sandstrom | 128/207.17 |

FOREIGN PATENT DOCUMENTS 669840  12/1938  Fed. Rep. of Germany ...... 128/207.14

Primary Examiner—Hiram Bernstein
Attorney, Agent, or Firm—Pearson & Pearson

[57] ABSTRACT

An endotracheal tube stabilizer avoids the pain of repeatedly stripping tape from the face of a patient, which affixes an endotracheal tube in position, and avoids damage caused by continuous pressure on one spot of a patient's mouth and teeth on a bit block by providing a straight mouthpiece with an outwardly projecting, integral fixation flange held in position by strands around the head which are received in holes in the fixation flange. The entire mouthpiece including the fixation flange is longitudinally slit with an opening substantially smaller than the outside circumference of the tube, so that the tube may be compressed for sidewise insertion.

4 Claims, 15 Drawing Figures

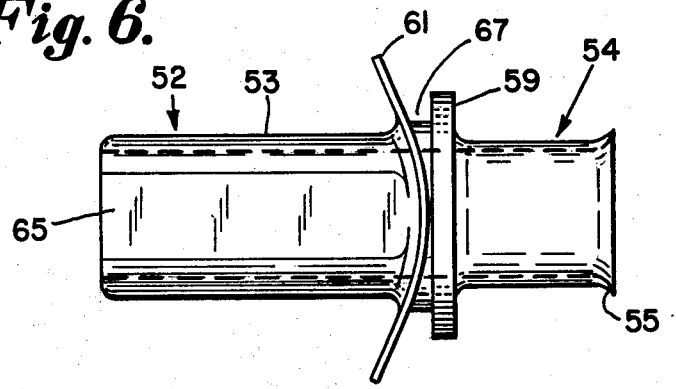
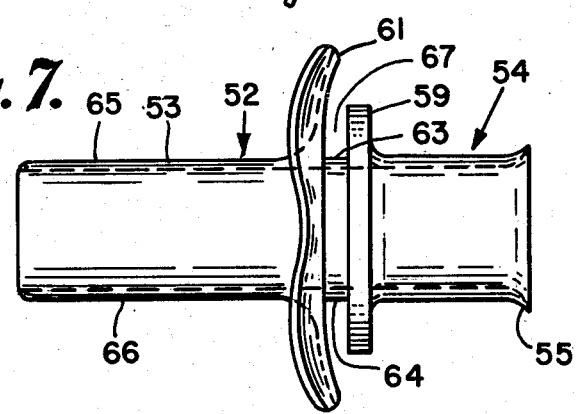
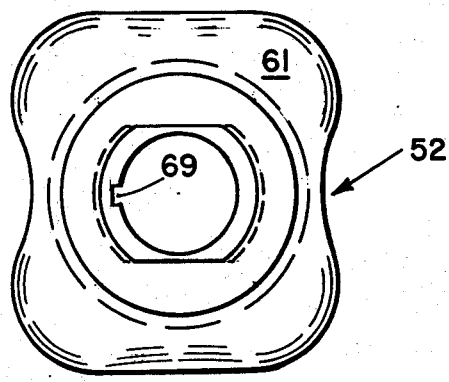

ENDOTRACHEAL TUBE STABILIZER

CROSS REFERENCE TO RELATED APPLICATION

This application is a continuation in part of my application, Ser. No. 023,652 filed Mar. 26, 1979.

BACKGROUND OF THE INVENTION

Endotracheal tube holders, clamps or retainers have long been known and have usually consisted of a faceplate, tied by a strap around the back of the patient's head, and covering the mouth area of the patient, there being a single aperture in the faceplate for receiving the endotracheal tube. Such devices are disclosed in U.S. Pat. No. 2,820,457 to Phillips of Jan. 21, 1958 wherein the faceplate is a flange integral with the mouthpiece and bite block and in U.S. Pat. No. 2,908,269 to Cheng of Oct. 13, 1959 wherein the faceplate has a tubular integral bite block on the side and an open slot on the other side for the tube.

The Cheng device provides a slot opening of greater outside circumference than that of a rigid tube so that a locking plate, locking arm and locking spring are required to retain the tube in the slot.

The prior art also reveals a line of clamp type faceplates for clamping on an endotracheal tube as disclosed in U.S. Pat. No. 3,602,227 of Aug. 31, 1971 and No. 3,760,811 of Sept. 25, 1973 to Andrew wherein the two sections of the clamp lock together around the tube but must be broken to remove the tube. A pivoted jaw type clamp is disclosed in U.S. Pat. No. 3,993,081 to Cussell of Nov. 23, 1976 wherein there may be two holes for two tubes but the device makes use of adhesive tape on the skin of the patient which applicant has found to be objectionable.

It is also known to provide a curved, elongated, airway, having a lateral slot opening to permit sidewise insertion of a tube before insertion of the airway into the trachea as in U.S. Pat. No. 4,068,658 to Berman of Jan. 17, 1978. Also to provide a straight, tooth shield member of unsplit tubular cross section with a side support of generally U-shaped configuration for receiving a medical instrument as disclosed in U.S. Pat. No. 4,167,946 to Sundstrom of Sept. 18, 1979.

However, these patents do not disclose any means for stabilization of the tube in the mouth laterally or side wise and presumably must be taped directly onto the skin of the patient's face.

SUMMARY OF THE INVENTION

In this invention, an endotracheal tube stabilizer is provided which is not affixed to the skin of the patient, the removal thereof for shifting the position of the bite block, having been found to be extremely painful especially for a whiskered male adult. The stabilizer of the invention as claimed in my said application, Ser. No. 023,652 comprises a relatively wide faceplate of soft flexible plastic material with one, or sometimes two, integral ears on each side by which it can be flexed to conform to the patient's face and tied by tapes, strands, etc. around the patient's head.

The faceplate includes a central, wide, closed-end slot, substantially equal in width to the width of the patient's mouth and the slot having spaced upper and lower edges generally in parallelism and equally spaced apart. Integral, oppositely disposed pairs of bendable prongs are provided along the edges of the slot to define a right side aperture, a central aperture and a left side aperture.

A mouthpiece, preferably of plastic is mounted for sidewise sliding movement in the slot, held in place by front and rear flanges and having an axial bore generally normal to the face plate, a tubular bite block portion and a tubular guide portion.

The portion of the tubular mouthpiece between the front and rear flanges is flat at top and bottom to slide in the slot but to prevent turning.

Preferably the mouthpiece of the stabilizer of the invention is not only slidable sidewise in a central, wide, closed end, slot in the faceplate but itself is provided with a flared, full length, slot having an opening which is substantially smaller than the outside circumference of the compressible tube. Thus the tube may be compressed to pass the opening so that expansion to normal circumference retains the tube in the slot.

This preferred form of mouthpiece is straight and provided with an integral, outwardly projecting, fixation flange, in the intermediate portion of its length, the full length slot flaring out into the flange and there being tape holes in each quadrant around the flange for fastening tapes extending around the head of the patient.

BRIEF DESCRIPTION OF THE DRAWING

FIG. 6 is a top plan view of an enlarged scale, of the mouthpiece;

FIG. 7 is a side elevation, similar to FIG. 6 of the mouthpiece;

FIG. 8 is a rear elevation of the mouthpiece on the scale of FIGS. 6 and 7;

DESCRIPTION OF THE PREFERRED EMBODIMENT

Figure 1:
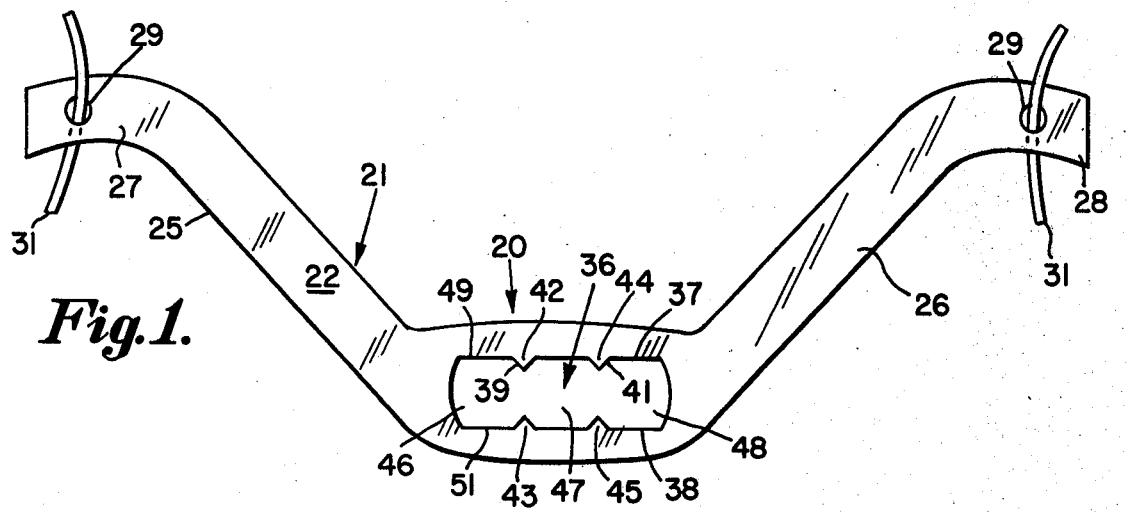
FIG. 1 is a front elevation of one embodiment of the flexible faceplate of the invention.
Figure 2:
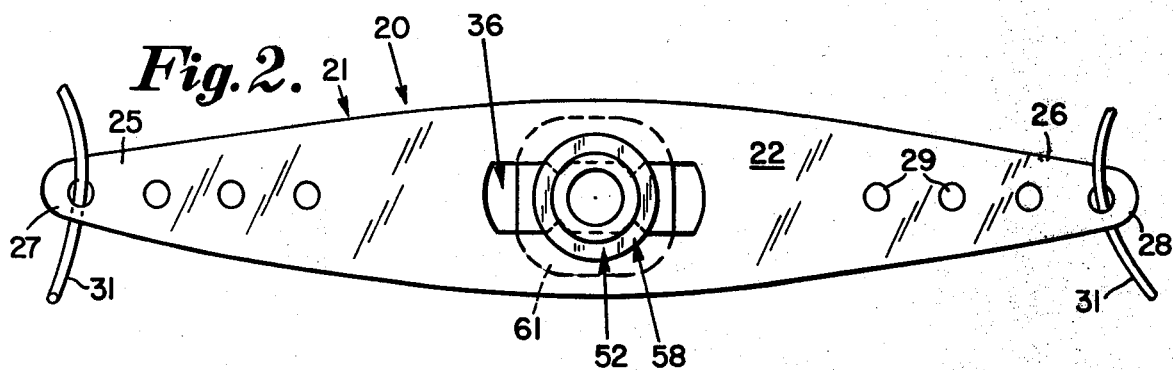
FIG. 2 is a view similar to FIG. 1 showing the tubular mouthpiece of the invention retained in the slot in another embodiment of the faceplate.
Figure 3:
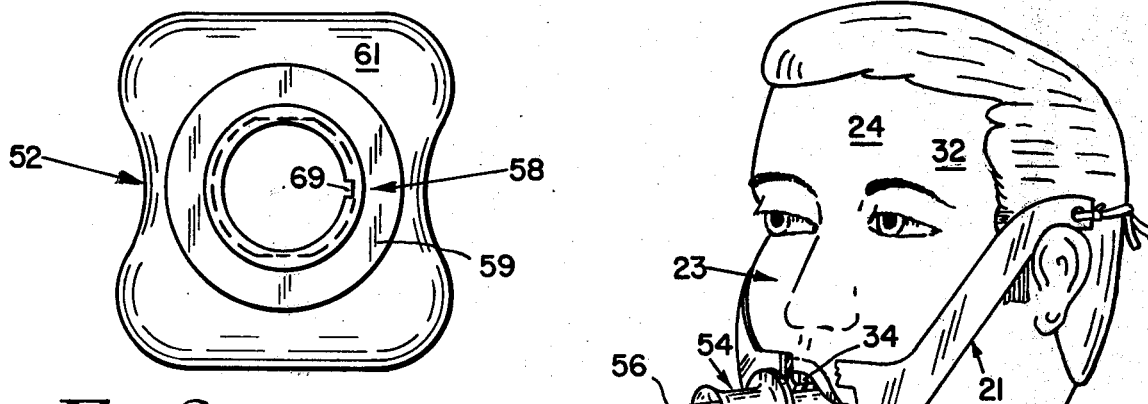
FIG. 3 is a front elevation of the mouthpiece.
Figure 4:
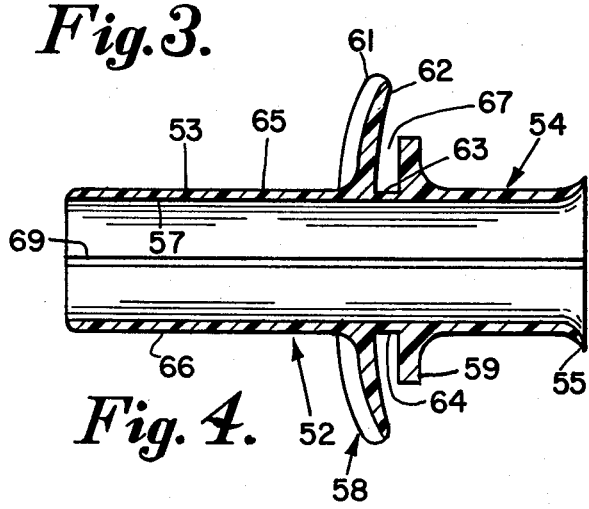
FIG. 4 is a side elevation in half section of the mouthpiece.
Figure 5:
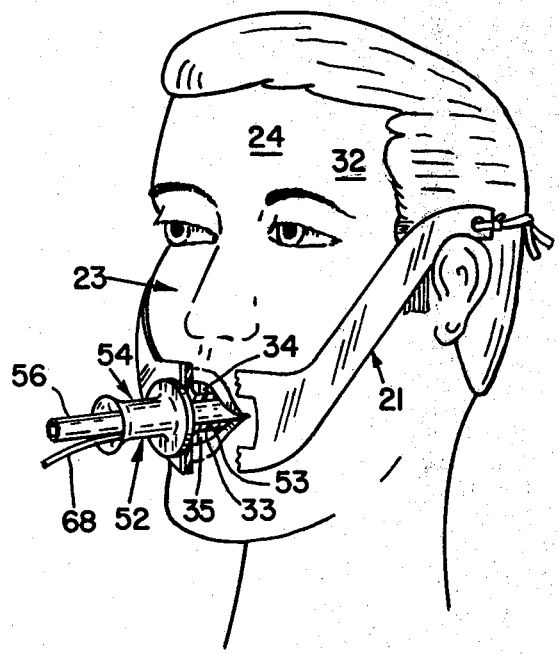
FIG. 5 is a perspective view of the device in use.

The endotracheal tube stabilizer 20, of the invention includes the faceplate, flange, or collar 21, which is preferably of soft, flexible, resilient plastic 22 so that it will easily conform to the configuration of the face 23 of a patient 24. Faceplate 21 includes at least one pair of integral ears 25 and 26 each of substantial length and terminating in tips 27 and 28, each having holes such as 29 for strands 31 of ribbon, tape or the like for tying around the head 32 of the patient 24 to position the faceplate over the mouth 33 of the patient. The faceplate 20 is of predetermined width at least equal to the width of the mouth 33 of a patient 24 and is of predetermined height at least sufficient to abut and cover the mouth 33, upper front teeth 34 and lower front teeth 35.

Faceplate 21 is provided centrally with a wide slot 36 which is substantially coextensive in width with the width of the mouth 33 of a patient and which includes upper edge 37 and lower edge 38 which are equally spaced apart and in substantial parallelism except for two pairs 39 and 41 of oppositely disposed integral flexible, resilient prongs such as 42, 43, 44 and 45. The pairs 39 and 41 of prongs divide the slot 36 into a left side aperture 46, a central aperture 47 and a right side aperture 48, each with straight, or flat, upper and lower walls, or edges, as at 49 and 51 which are in parallelism.

The tubular mouthpiece 52 of the invention includes a tubular portion 53, forming a "bite block", which portion enters the mouth 33 of the patient 24 for receiving the bite of the upper front teeth 34 and the lower front teeth 35 and includes a tubular guide portion 54 extending away from the mouth 33 and flared at 55 for receiving and guiding an endotracheal tube 56. The mouthpiece 52 includes an axial bore 57 of uniform diameter which extends generally normal to faceplate 21 and which slidably receives the tube 56.

Flange means 58 is provided for retaining the mouthpiece 52 in slot 36 while permitting selective sidewise movement therein. Means 58 includes a front flange 59 of circular flat configuration spaced from a rear flange 61 of generally square configuration, flange 61 being concave curved in plan to conform to the curve of the teeth of the patient. The central portion 62 of rear flange 61 is spaced from the front flange 59 a distance substantially equal to the thickness of the material 22 of the faceplate so as to prevent forward or rearward tilting of the mouthpiece relative to the faceplate while enabling side wise sliding movement of the mouthpiece in the slot 36. The upper surface 63 and the lower surface 64 of the portion of mouthpiece 52 between the flanges 59 and 61 are each flat and parallel to each other so that the mouthpiece will slide side wise in slot 36 but will not turn on its axis.

The upper surface 65 and the lower surface 66 of the bite block tubular portion 53 are also flat and parallel to each other to conform to the flat configuration of the upper and lower front teeth 34 and 35.

In operation the mouthpiece 52 is affixed in the slot 36 of faceplate 21 by flexing the material of the faceplate, in the area of the slot, aound the front flange 59 until the faceplate is received in the gap 67 between flange 59 and flange 61. With the bite block portion 53 of the mouthpiece inserted in the patient's mouth, the ears of the faceplate are then bent to conform to the shape of the patient's face and the faceplate tied around the patient's head by the strands 31. The mouthpiece may start in the central aperture 47 and the endotracheal tube 56 slid into the bore 57 and down into the trachea. A cuff not shown but well known may then be inflated by the conduit 68 extending along a shallow groove 69 in the wall of the axial bore 57 in a well known manner. The endotracheal tube 56 is usually taped to the guide portion 54 of the mouthpiece to slide with the mouthpiece into side aperture 48 or 49 when the attendant or physician feels that the patient's mouth and teeth need relief. The other unused apertures permit insertion of other tubes into the mouth for any desired purpose.

Figure 11:
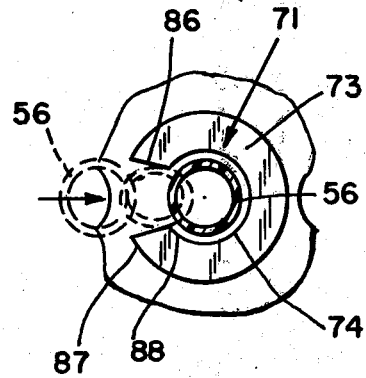
FIG. 11 is a diagrammatic front end elevation showing a tube in dotted lines being compressed to pass through the slot opening.
Figure 12:
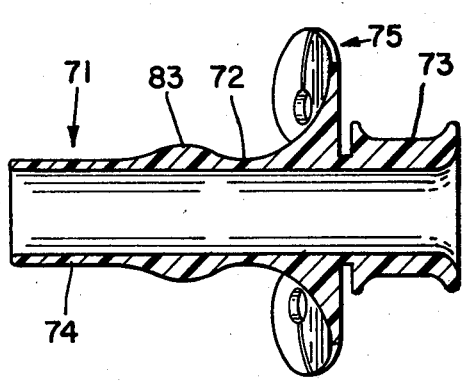
FIG. 12 is a side elevation of the slotted mouthpiece of FIG. 10, in half section.
Figure 13:
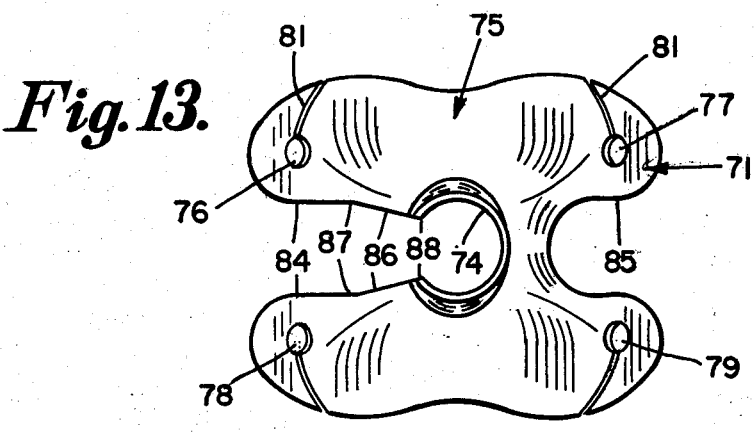
FIG. 13 is rear end elevation.
Figure 14:
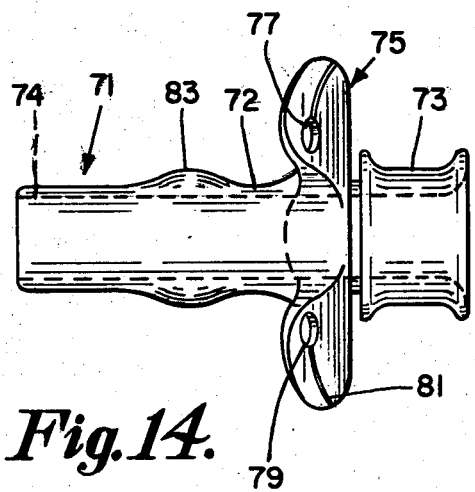
FIG. 14 is a top plan view of the slotted mouthpiece.
Figure 15:
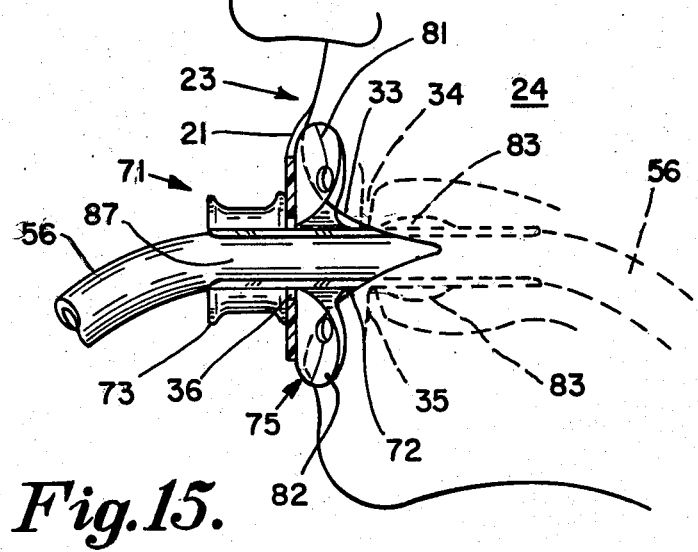
FIG. 15 is a diagrammatic side elevation, partly in section, showing the stabilizer of FIGS. 9–14 in use.

As shown in FIGS. 9–15 a tubular mouthpiece 71 of preferred construction corresponds to tubular mouthpiece 52 in having a tubular portion 72 forming the "bite block", a tubular guide portion 73 and an axial bore 74 of predetermined, uniform diameter which slidably receives a tube 56 of slightly less predetermined uniform diameter. The tube 56 is of resilient compressible material such as rubber or plastic so that it may be compressed to oval cross section as shown in FIG. 11.

Mouthpiece 71 includes the integral flange means 75, corresponding to flange means 58, for retaining the mouthpiece 71 in slot 36 while permitting selective side wise movement therein. However, holes 76, 77, 78 and 79 are provided in each corner of the flange means 75, each having a curved entrance slot such as 81 leading thereinto to enable tapes 31 to be directly attached if desired, without the use of a faceplate 21. The outwardly projecting, fixation flange 82 of flange means 75, corresponding to rear flange 61 is similarly curved to take the shape of the face and teeth of the patient 24.

The tubular portion 72 of mouthpiece 71, includes a elongated, annular, protruberance 83, extending therearound and which co-operates with fixation flange 82 in assisting the patient 24 to retain the bite block between his teeth without tendency to slip, slide or dislodge.

The fixation flange 82 of flange means 75 is provided with a recess 84 and 85, each on an opposite side thereof. The entire mouthpiece 71 is provided with a full length, tapered, slot 86 flaring from an outer opening 87, in flange 82, considerably greater than the outside diameter of the compressible tube 56 to the inner opening 88, at the bore 74, which is substantially smaller than the outside diameter of tube 56.

It will be seen that the mouthpiece 71 may be used without a face plate by slipping tapes 31 into slots 81 and thence into tape holes, 76, 77, 78 and 79 (FIG. 13) and tying the tapes around the head of the patient. The patients teeth are clamped on the bite block portion 72 and the tube 56 may be quickly locked in bore 74 by sliding it laterally through tapered slot 87, compressing it at opening 88 and allowing normal expansion to retain the tube from side wise movement. (FIG. 11). While the tube 56 is shown of smaller diameter than the bore 74 in FIG. 11, to enable longitudinal movement inwardly and outwardly of the mouthpiece when desired, it may prove desirable in some cases to have the tube make a close friction fit in the bore so that it will not slide in and out easily but can be inserted and withdrawn laterally through slot 87 with ease and rapidity.

Figure 9:
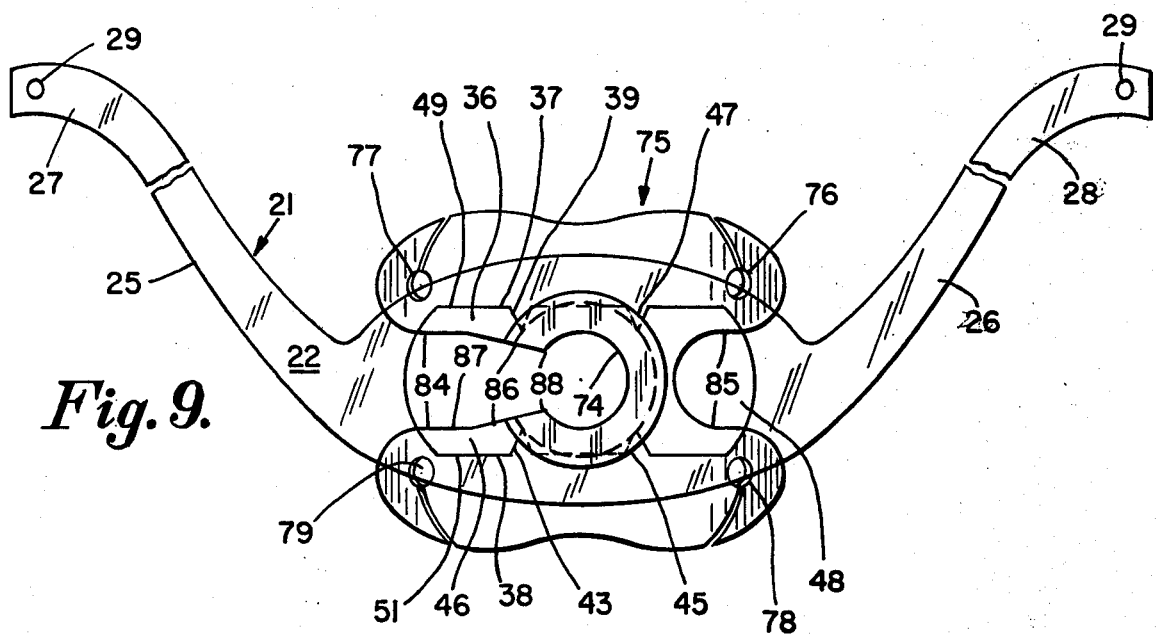
FIG. 9 is a view similar to FIG. 2 showing a slotted mouthpiece of the invention in the slotted faceplate of the invention.
Figure 10:
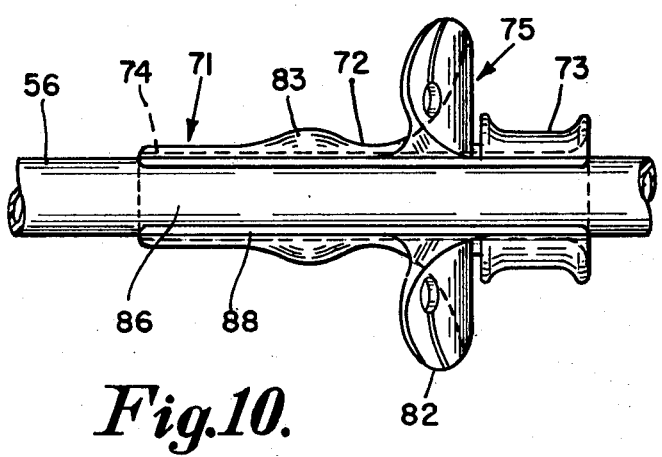
FIG. 10 is a side elevation of the slotted mouthpiece.

Thus when the tube 56 will not slide easily out of bore 74, and mouthpiece 71 is mounted in a faceplate 21, as shown in FIG. 9, the mouthpiece may be moved side wise past prongs 39 or 41 to left side aperture 46 or to right side aperture 48 or the tube may be compressed to pass opening 88 and slide freely in opening 87 of slot 86 for longitudinal shift or removal.

I claim:

1. An endotracheal tube stabilizer for retention of a tube of compressible material having a predetermined, substantially uniform, outside diameter, said stabilizer comprising:
   a mouthpiece having an elongated, straight generally tubular, body with an axial bore of predetermined diameter for receiving said tube, said mouthpiece having;
   an integral, annular fixation flange in an intermediate portion of the length thereof, projecting outwardly therearound, an elongated bite block portion in rear of said flange and an elongated guide portion in front of said flange;

said mouthpiece having a laterally open slot extending the full length thereof from said bit block portion through said flange and intermediate portion and to said guide portion and flaring from an outer opening in said flange of greater dimension than the outer diameter of said tube to an inner opening, at said bore, of less dimension than the outer diameter of said tube; and tape holes in said fixation flange and tape in said holes fixing said mouthpiece in the mouth of a patient.

2. An endotracheal tube stabilizer as specified in claim 12 wherein:

said fixation flange for fixing said mouthpiece in the mouth of a patient includes a tape hole in each quadrant thereof, each hole having an access slot for receiving a fastening tape.

3. An endotracheal tube stabilizer for retention of a tube of compressible material having a predetermined, substantially uniform, outside diameter, said stabilizer comprising:

a mouthpiece having an elongated, straight generally tubular, body with an axial bore of predetermined diameter for receiving said tube;

said mouthpiece having an intermediate portion with an outwardly projecting, fixation flange having holes for the direct attachment of fastening tapes, an elongated bite block portion in rear of said intermediate portion and an elongated guide portion in front of said intermediate portion;

said mouthpiece having a laterally open slot extending the full length thereof from said bit block portion through said intermediate portion to said guide portion and flaring from an outer opening of greater width than the outer diameter of said tube in said flange to an inner opening, at said bore, of less width than the outer diameter of said tube; and fastening tapes in said holes for securing said mouthpiece in the mouth of a patient without the use of adhesive tape 4. A stabilizer as specified in claim 3 wherein:

said fastening holes in said fixation flange are each in one of the four quadrants around said flange.

* * * * *

UNITED STATES PATENT OFFICE
CERTIFICATE OF CORRECTION

Patent No. 4,270,529      Dated June 2, 1981

Inventor(s) Rudolph Muto

It is certified that error appears in the above-identified patent and that said Letters Patent are hereby corrected as shown below:

In Claim 2, line 2, "Claim 12" should read "Claim 1".

Signed and Sealed this

Twenty-fifth Day of August 1981

[SEAL]

*Attest:*

*Attesting Officer*

GERALD J. MOSSINGHOFF

*Commissioner of Patents and Trademarks*